United States Patent [19]

Brittenham et al.

[11] Patent Number: 5,059,395

[45] Date of Patent: Oct. 22, 1991

[54] PARTICLE ANALYZING APPARATUS

[75] Inventors: Gary M. Brittenham, Euclid; Christopher J. Allen, Cleveland, both of Ohio; Tokuhiro Okada; Keiji Fujimoto, both of Hyogo, Japan

[73] Assignee: Toa Medical Electronics Co., Ltd., Kobe, Japan

[21] Appl. No.: 269,138

[22] Filed: Nov. 9, 1988

[30] Foreign Application Priority Data

Mar. 30, 1988 [JP] Japan .................................. 63-77365

[51] Int. Cl.$^5$ ............................................ G01N 15/02
[52] U.S. Cl. ........................................ 422/73; 377/11; 356/335
[58] Field of Search ............................ 422/73; 377/11; 356/335

[56] References Cited

U.S. PATENT DOCUMENTS 4,491,926  1/1985  Okada et al. .
4,596,464  6/1986  Hoffman et al. ...................... 377/11

Primary Examiner—David L. Lacey
Assistant Examiner—Abanti B. Singla
Attorney, Agent, or Firm—Fitch, Even, Tabin & Flannery

[57] ABSTRACT

In particle analysis applied to blood cells, use is made of a distinguishing parameter which is the ratio of pulse height to pulse width derived from individual pulses generated in response to detection of corresponding individual particles. The distribution of the distinguishing parameter is plotted on a distribution of pulse height and pulse width, and a three-dimensional display of pulse height, pulse width and the distinguishing parameter is used in analyzing the particles.

2 Claims, 20 Drawing Sheets

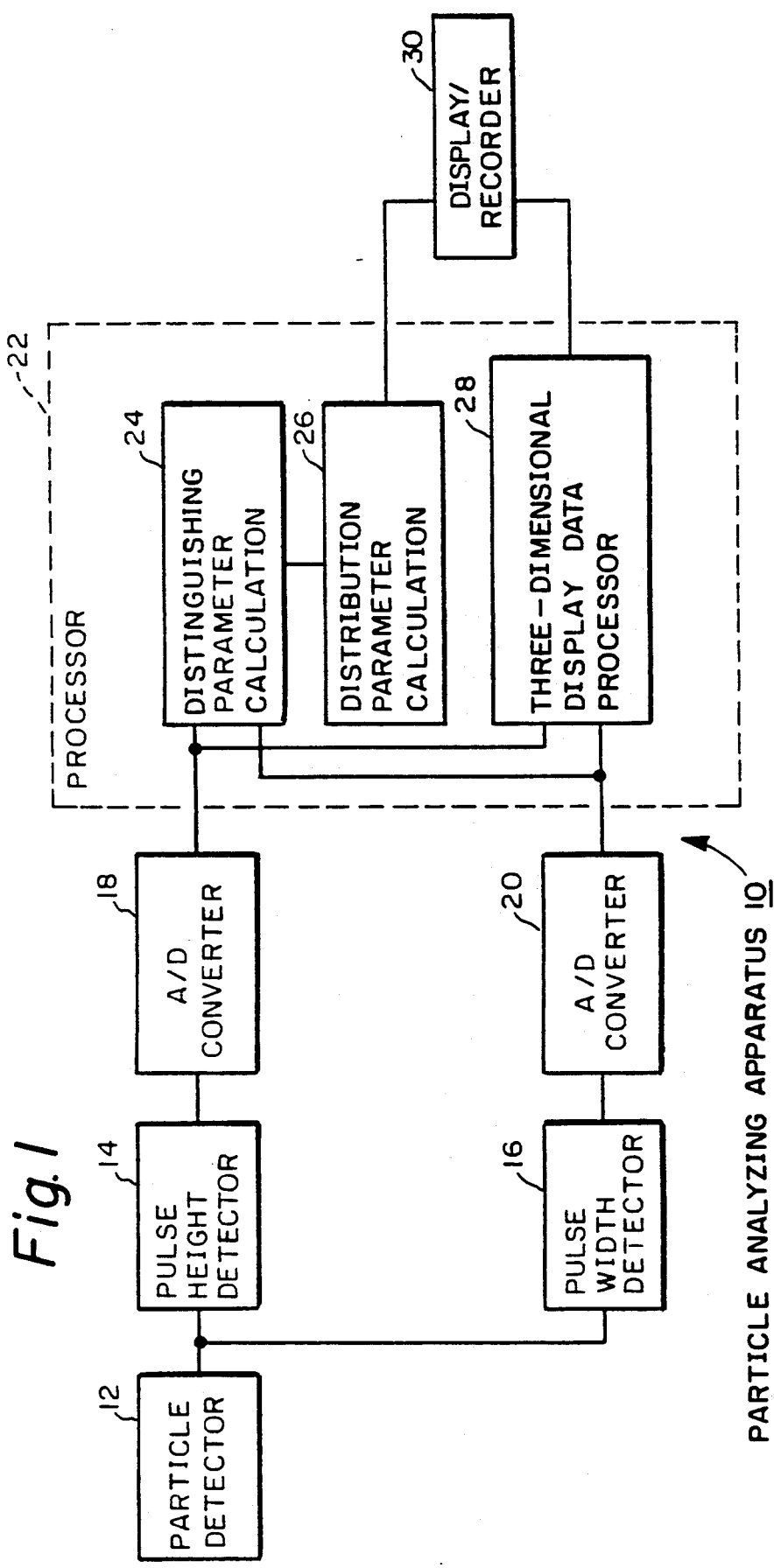

Fig. 2(a) Fig. 3(a)
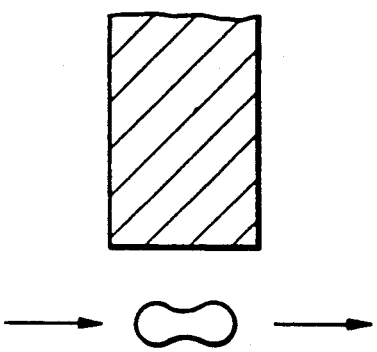 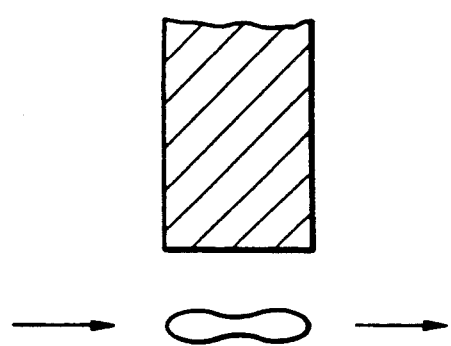
Fig. 2(b) Fig. 3(b)
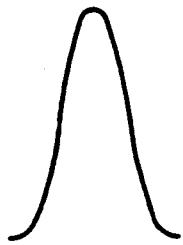 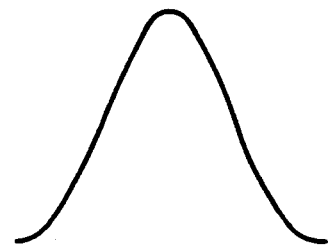

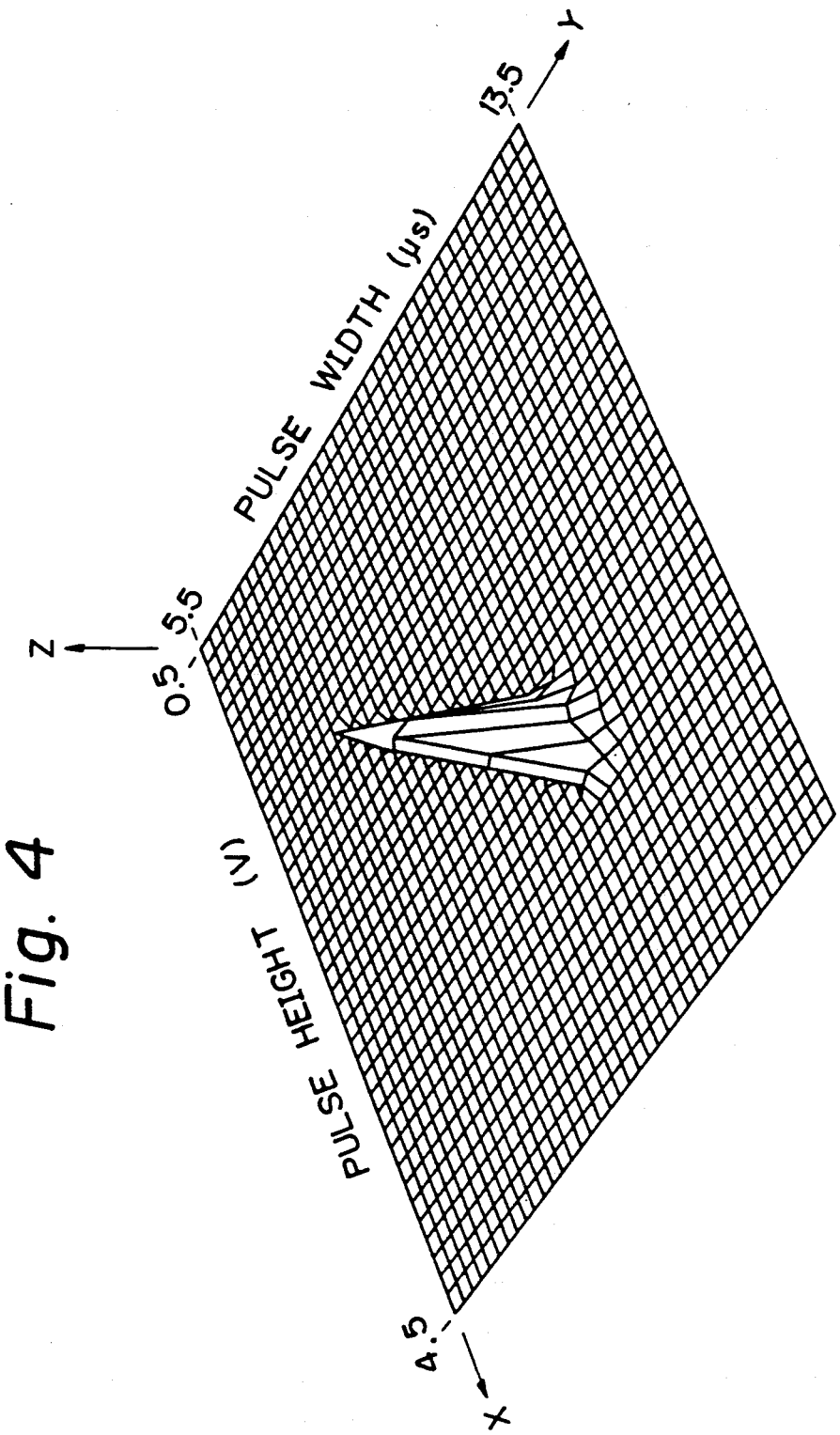

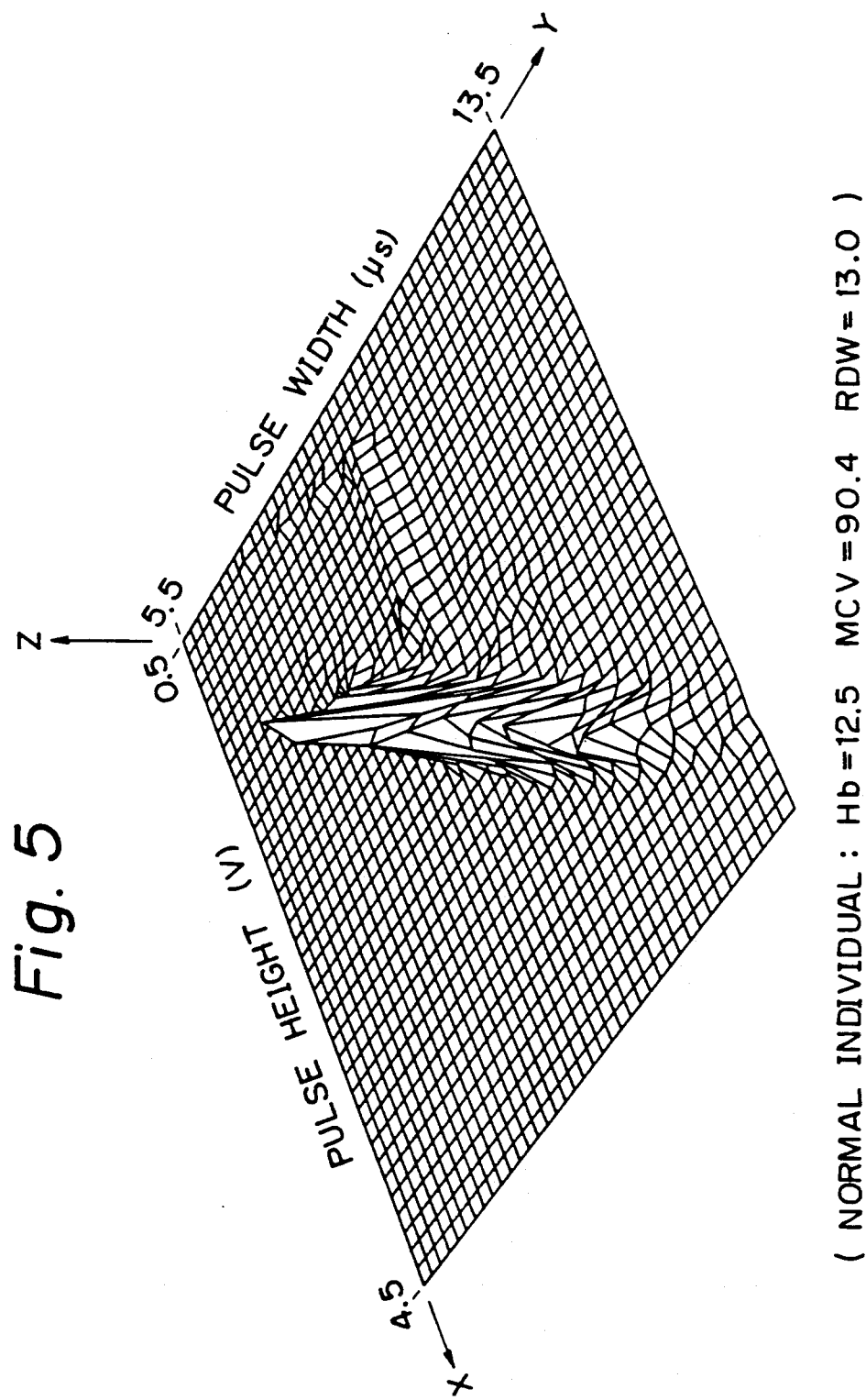

(PATIENT WITH MILD ANEMIA CAUSED BY CHRONIC DISORDER:
Hb=10.7  MCV=85.7  RDW=14.1 )

(PATIENT WITH SICKLE CELL ANEMIA: Hb = 7.9  MCV = 91  RDW = 23.3)

( BETA THALASSEMIA : Hb=14.6  MCV=70  RDW=14.4 )

(PATIENT WITH EARLY IRON-DEFICIENCY ANEMIA: Hb =12.7
MCV = 70.4  RDW=14.5)

(PATIENT WITH MILD FOLATE DEFICIENCY ANEMIA: Hb = 10.6
MCV = 105.7   RDW = 16.1 )

(PATIENT WITH CHRONIC RENAL FAILURE RECEIVING CYTOTOXIC CHEMOTHERAPY: Hb = 8.1  MCV = 104.7  RDW = 20.2)

(PATIENT WITH HEMOLYTIC ANEMIA, RED CELL 5'-NUCLEOTIDASE DEFICIENCY: Hb=11.1  MCV=115  RDW=14.3 )

PARTICLE ANALYZING APPARATUS

BACKGROUND OF THE INVENTION

This invention relates to a particle analyzing apparatus which provides information valuable for use in clinical diagnosis or the like by introducing a parameter which clearly shows the characterizing features of a particle in the analysis of particles such as blood cells.

So-called particle size distributions, in which a distribution of the sizes of particles under measurement is obtained and expressed as a histogram of the frequency of occurrence of particles with respect to size, find use in the industrial field and in various other fields as well.

Automatic particle analyzers are adapted to pass particles one at a time through a very small detecting area and detect electric signal pulses, each of which corresponds to the size of a discrete particle passing through the detecting area. Since such an apparatus makes it possible to obtain a particle size distribution very simply from information relating to the heights of the pulses, the fields of application of the apparatus has broadened considerably.

A so-called sheath-flow analyzer for measuring particles by passing them through the center of a detecting area, in a precise ordered array of a single file, is utilized also in the field of clinical diagnosis. This analyzer provides a highly accurate particle size distribution and is being positively applied in clinical diagnosis by measuring the particle size distribution of red blood cells, white blood cells and platelets in blood.

A problem with the prior art is that since use is made solely of particle size information, i.e., pulse height information, there is a limitation upon the usefulness of a particle size distribution in that, when attempting to diagnose a particular type of anemia, a particle size distribution does not make it possible to clearly distinguish between, say, iron-deficiency anemia and thalassemia.

An apparatus adapted to utilize pulse width as information, in addition to pulse height information, has been proposed. An apparatus of this kind has been disclosed in Japanese Patent Application Public Disclosure (KOKAI) No. 230139/1984, by way of example. The apparatus is capable of identifying blood cell type, or of distinguishing between blood cells and noise, by utilizing information relating to pulse height and width. Nevertheless, the disclosure is silent upon the aforementioned problem relating to analysis of blood cell particle size distribution, and does not mention any improvements in blood cell particle size distributions. In addition, nowhere does the disclosure describe a technique for applying an improved blood cell particle size distribution to diagnosis for identifying a particular type of anemia by name.

Japanese Patent Application Public Disclosure (KOKAI) Nos. 79834/1984 and 81536/1984 disclose an apparatus equipped with circuitry for detecting pulse height, area and width, in which logarithms, products, ratios, differences, sums or combinations thereof are processed with regard to each output produced. However, these disclosures in fact do nothing more than describe signal processing circuits and are silent upon techniques for applying the art to the clinical field, as for the purpose of diagnosing types of anemia by name.

More specifically, all of the aforementioned disclosures differ from the present invention in terms of their purpose, and therefore only describe that pulse width is merely detected as additional information to supplement pulse height information. These disclosures are not concerned with the true significance of detecting pulse width and the usefulness of such detection.

SUMMARY OF THE INVENTION

The present invention is based on the finding that the width of a pulse, detected when a particle passes through a minute aperture in a particle analyzer, possesses valuable information that reflects the characteristics of the particle. An object of the invention is to provide a particle analyzing apparatus capable of contributing to clinical diagnosis or the like by measuring, in addition to pulse height (which reflects particle size), pulse width reflective of particle characteristics, calculating the ratio for pulse height to pulse width, and introducing a useful distinguishing parameter in particle analysis.

According to the present invention, the foregoing object is attained by providing a particle analyzing apparatus comprising:

A. particle detecting means for generating pulses corresponding to individual particles;
B. means for detecting the height and width of the individual pulses;
C. means for detecting a distinguishing parameter from the detected height and width of the individual pulses;
D. means for calculating a distribution parameter of the distinguishing parameter; and
E. three-dimensional data display means.

The distinguishing parameter preferably is the ratio of pulse height to pulse width, and coefficient of variation is particularly preferred as the distribution parameter.

In accordance with the particle analyzing apparatus of the present invention, pulse width is detected in addition to pulse height. Generally, pulse height is considered to reflect the size of a particle in particle detecting means. In particular, if the particle detecting means operates by detecting a change in electrical resistance, specifically, a change in the electrical resistance of a minute aperture when a particle floating in an electrolytic suspension passes through the aperture, and if the sheathflow method of measurement is adpoted, pulse height will be accurately proportional to particle volume.

It should be noted that even when particles having the same volume pass through a minute aperture, pulse width differs depending upon the ease with which the particles undergo deformation. More specifically, when a particle with little deformability passes through a minute aperture, as shown in FIG. 2(a), a pulse with a small width is generated, as shown in FIG. 2(b). Conversely, when a readily deformable particle passes through a minute aperture, as shown in FIG. 3(a), a pulse with a large width is generated, as shown in FIG. 3(b).

If the particle is a red blood cell, the more flexible the cell membrane and the lower the hemoglobin concentration in the red blood cell, the more easily the particle undergoes deformation. Since the cell membrane flexibility and hemoglobin concentration of a healthy individual differ from those of a patient with anemia, and since there are also differences in cell membrane flexibility and hemoglobin concentration even among anemic patients, depending upon the type of anemia, information useful in accurately diagnosing the anemia that corresponds to a particular disorder can be provided by detecting pulse width.

Pulse width information contains, to some extent, information relating to particle size. However, if the pulse width of each individual pulse is divided by pulse height, it is possible to obtain the characteristics of a particle per unit volume, namely true particle characteristics that are not influenced by particle size. Accordingly, further advantages are obtained when anemia is diagnosed based on particle characteristics. It should be noted that since information, substantially the same as that mentioned above is obtained, even if pulse height is divided by pulse width rather than vice versa, whether pulse width/height or pulse height/width is adopted as the distinguishing parameter is suitably selected, depending upon the ease with which the data can be processed within the apparatus.

If the apparatus is equipped with three-dimensional display data processing means, it is possible to obtain plots of a three-dimensional distribution in which a frequency histogram is expressed in a direction perpendicular to a plane having two axes along which pulse height and width are plotted, and much more information can be obtained than is acquired from the conventional plot of two-dimensional particle size distribution. As a result, it is possible to accurately distinguish between a patient with iron-deficiency anemia and one with thalassemia, unlike the prior-art arrangement in which these two types of anemia could not be identified using a mere particle size distribution. Accordingly, the invention represents a major contribution of clinical diagnosis.

BRIEF DESCRIPTION OF THE DRAWINGS

FIG. 1 is a block diagram illustrating an embodiment of a particle analyzing apparatus according to the present invention;

FIGS. 2(a) and 2(b) are schematic views illustrating the manner in which a readily deformable particle passes through a pore and a pulse generated at such time;

FIGS. 3(a) and (b) are schematic views illustrating the manner in which a particle exhibiting little deformability passes through a minute aperture and a pulse generated at such time;

FIGS. 4 through 14 are plots of three-dimensional distributions in which pulse height and pulse width serve as parameters, wherein:

FIG. 4 is a distribution based on latex particles;
FIG. 5 is a distribution based on the red blood cells of a healthy individual;
FIGS. 6 through 14 are distributions based on the red blood cells of patients with various types of anemia;
FIGS. 15 through 21 are plots of two-dimensional distributions in each of which (a) is a frequency distribution regarding pulse height, (b) is a frequency distribution regarding pulse width and (c) is a frequency distribution regarding pulse width/pulse height, wherein:

FIG. 15 is a distribution based on the red blood cells of a healthy individual; and
FIGS. 16 through 21 are distributions based on the red blood cells of patients with various types of anemia.

DESCRIPTION OF THE PREFERRED EMBODIMENT

Figure 6:
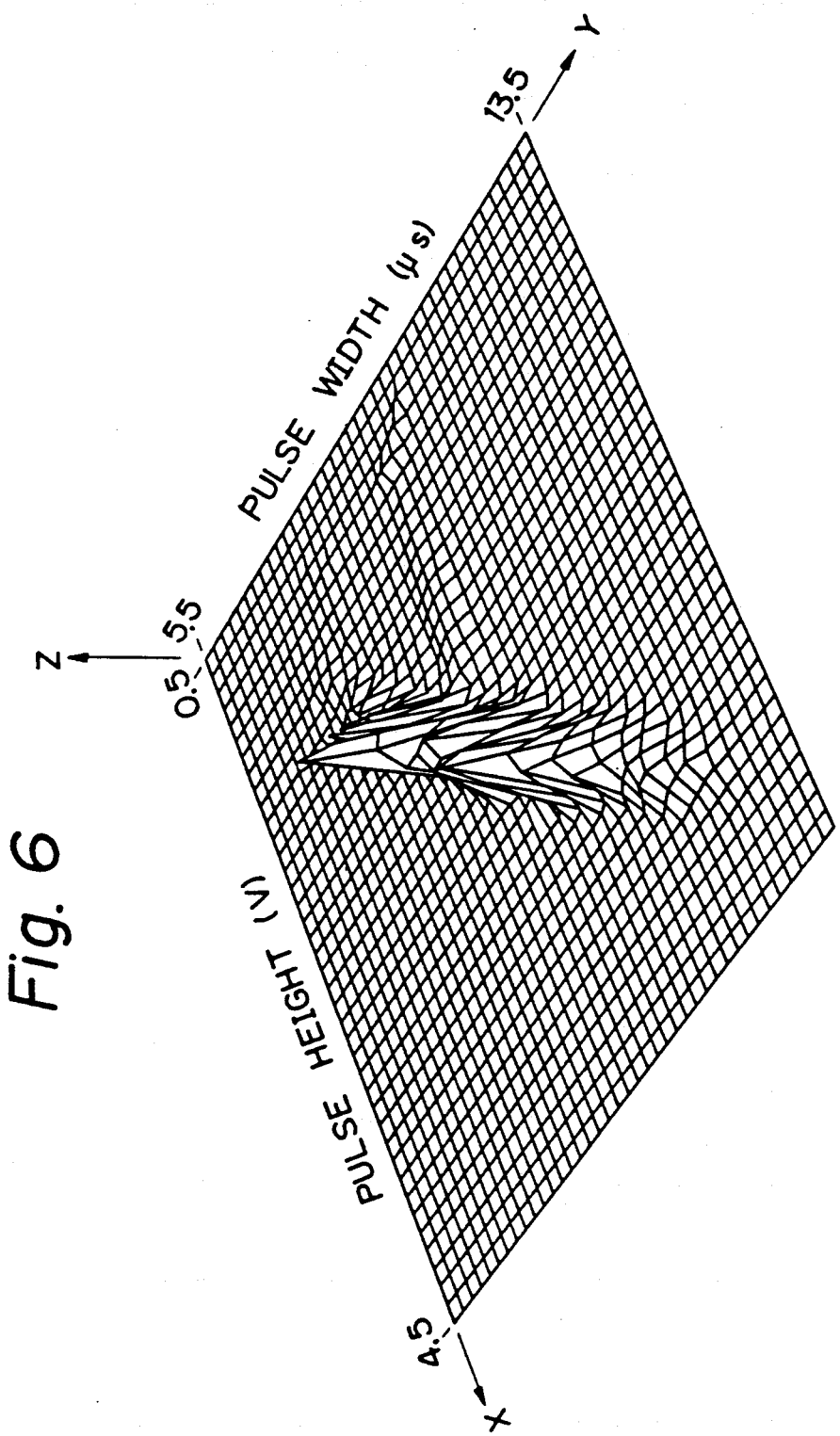

An embodiment of a particle analyzing apparatus according to the present invention, as well as an example of measurement using the apparatus, will now be described.

In the block diagram of FIG. 1, the apparatus 10 embodying the invention includes a particle detecting unit 12, having a particle detecting area (a minute aperture) through which particles such as cells pass one at a time, in response to which the detecting unit generates detection pulses corresponding to respective ones of the particles. These particle detection pulses from the detecting unit 12 are applied to pulse height detecting means 14 and pulse width detecting means 16. The pulse height detecting means 14 detects the crest value (an analog value) of the peak of each particle detection pulse, and the pulse width detecting means 16 detects the width (an analog value) of each particle detection pulse. The detected pulse height and width are subjected to an analog-to-digital conversion by respective A/D converting means 18, 20 before being delivered to processing means 22. Within the processing means 22, the values of pulse height and width are inputted to characteristic parameter calculating means 24, where various characteristic parameters are calculated. An example of a distinguishing parameter is the ratio of pulse height to pulse width of each pulse. The distinguishing parameter of each pulse is delivered to distribution parameter calculating means 26, where various distribution parameters relating to the distribution of the distinguishing parameter of each sample are calculated. Examples of the distribution parameters are mean value, standard deviation and coefficient of variation.

It is, of course, possible to adapt the distinguishing parameter calculating means 24 to calculate such already known parameters as mean red blood cell volume (MCV) and red blood cell distribution width (RDW) from pulse height information alone, as in the conventional particle analyzing apparatus.

The values of pulse height and width are also applied to three-dimensional display data processing means 28, which executes data processing to make possible three-dimensional displays of the kind exemplified by the examples of measurement shown in FIGS. 4 through 14.

The processing means 22 generally is constituted by a device, such as a computer, having a logical operation function. When required, the processing means 22 is provided with internal memory means for temporarily saving the values of pulse height and width, or data which is in the course of being processed in the distinguishing parameter calculating means 24, distribution parameter calculating means 26, and three-dimensional display data processing means 28, and for storing the results of processing.

The data processed by processing means 22 is delivered to display/recording means 30, so that the various distinguishing parameters and three-dimensional distributions may be displayed or printed out.

FIGS. 4 through 14 are plots of three-dimensional distributions showing the results obtained by measuring and analyzing particles with the apparatus of the illustrated embodiment. In each view, pulse height [in V (volt) units] is plotted along the X axis and covers a range of from 0.5 V to 4.5 V, with one graduation representing 0.1 V, and pulse width [in $\mu$s (microsecond) units] is plotted along the Y axis and covers a range from 5.5 $\mu$s to 13.5 $\mu$s, with one graduation representing 0.2 $\mu$s. In other words, the XY plane is indicated by a 40×40 grid. The Z axis indicates the frequency of appearance of particle having a pulse height and width corresponding to each grid point. Approximately 10,000 particles were measured in each view. Also, the measured values recorded at the bottom of each plot represent Hb samples, namely hemoglobin in mg/dl units, MCV, namely mean red blood cell volume in fl (femtoliter) units, and RDW, namely red blood cell distribution width in fl units. It should be noted that Hb was measured by an apparatus separate from that of analyzing apparatus of the invention.

FIG. 4 is a three-dimensional distribution obtained when latex particles were measured for calibration purposes. The purpose of this view is to control the precision of the apparatus.

FIGS. 5 through 14 are three-dimensional distributions obtained when red blood cells were measured as the specimen.

FIG. 5 is a distribution indicating the results obtained by measuring a sample from a normal or healthy individual. The distribution is narrow, free of distortion and oriented substantially along the diagonal of the XY plane.

Figure 7:
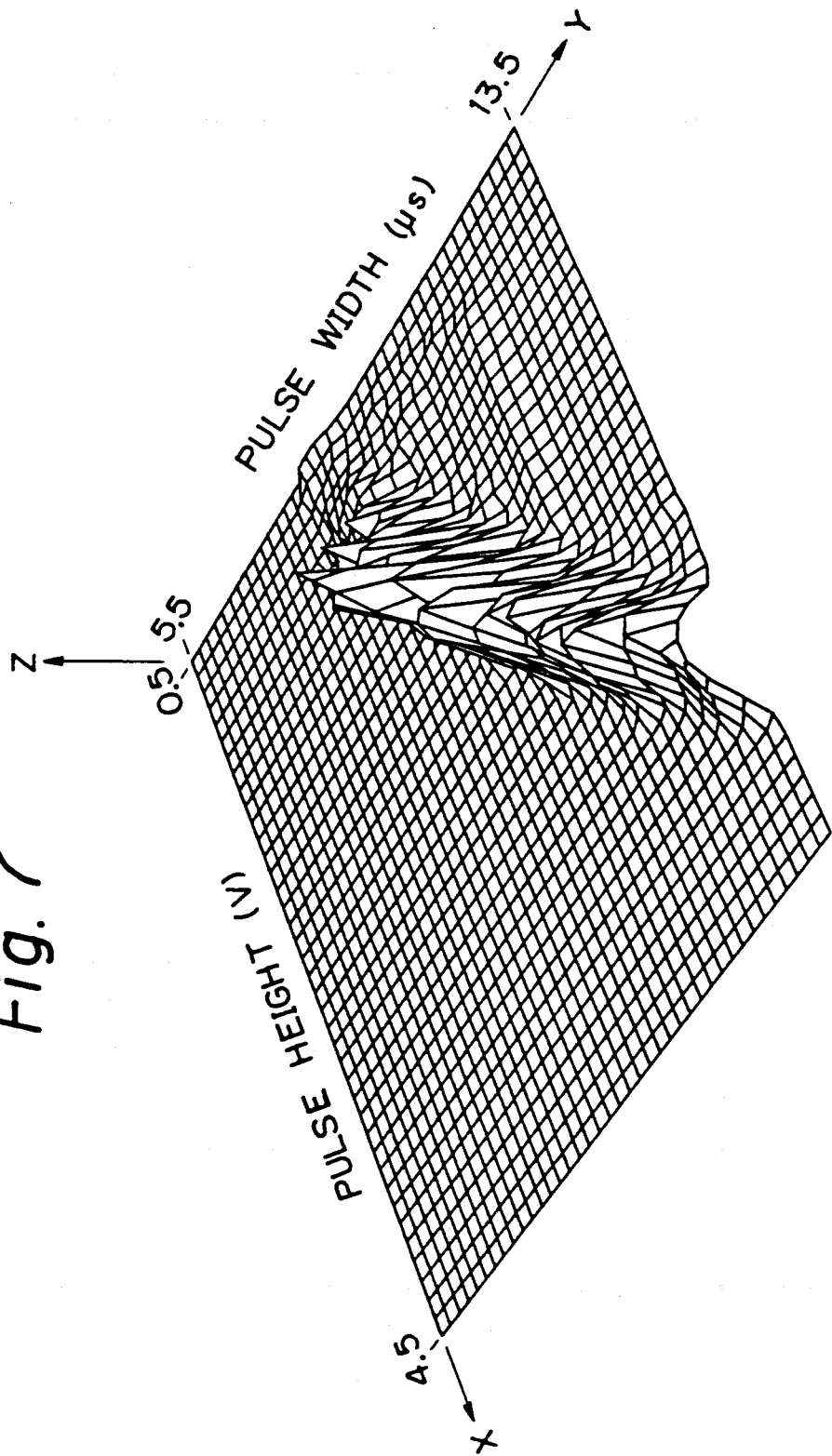

FIGS. 6 and 7 are distributions indicating the results obtained by measuring samples from patients with normocytic anemia. The distribution shown in FIG. 6 is that of a patient with mild anemia caused by a chronic disorder and substantially resembles the distribution for the healthy person shown in FIG. 5. The reason for this is that the characteristics of the red blood cell membrane and the hemoglobin concentration within the blood cells of this mildly anemic patient are substantially the same as those of the healthy patient. By contrast, the distribution of FIG. 7 is that of a patient afflicted with sickle-cell disease. In comparison with the distribution for a normal individual, the distribution here is distorted and shifted in its entirety to the right of the aforementioned diagonal.

Figure 8:
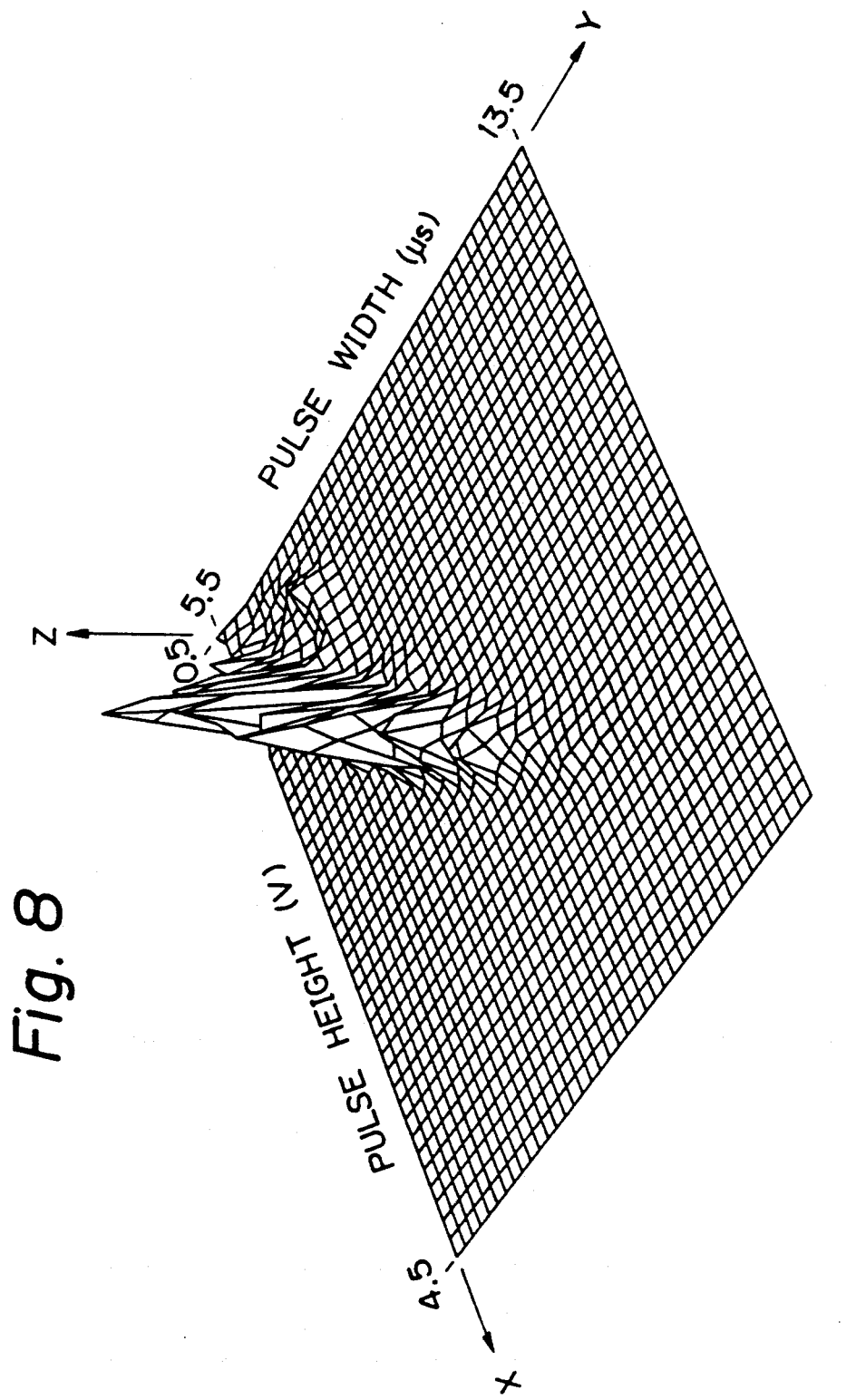
Figure 9:
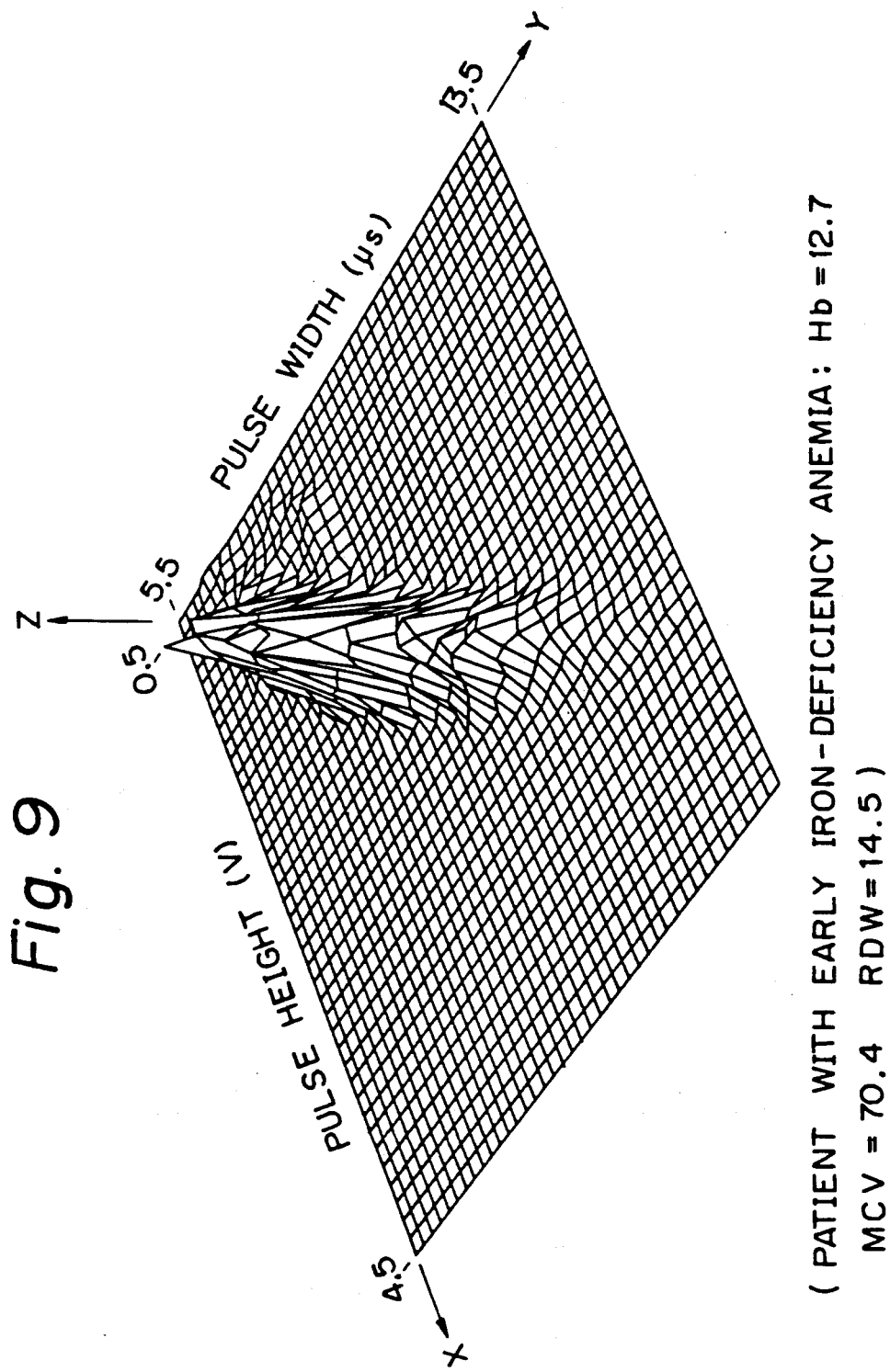
Figure 10:
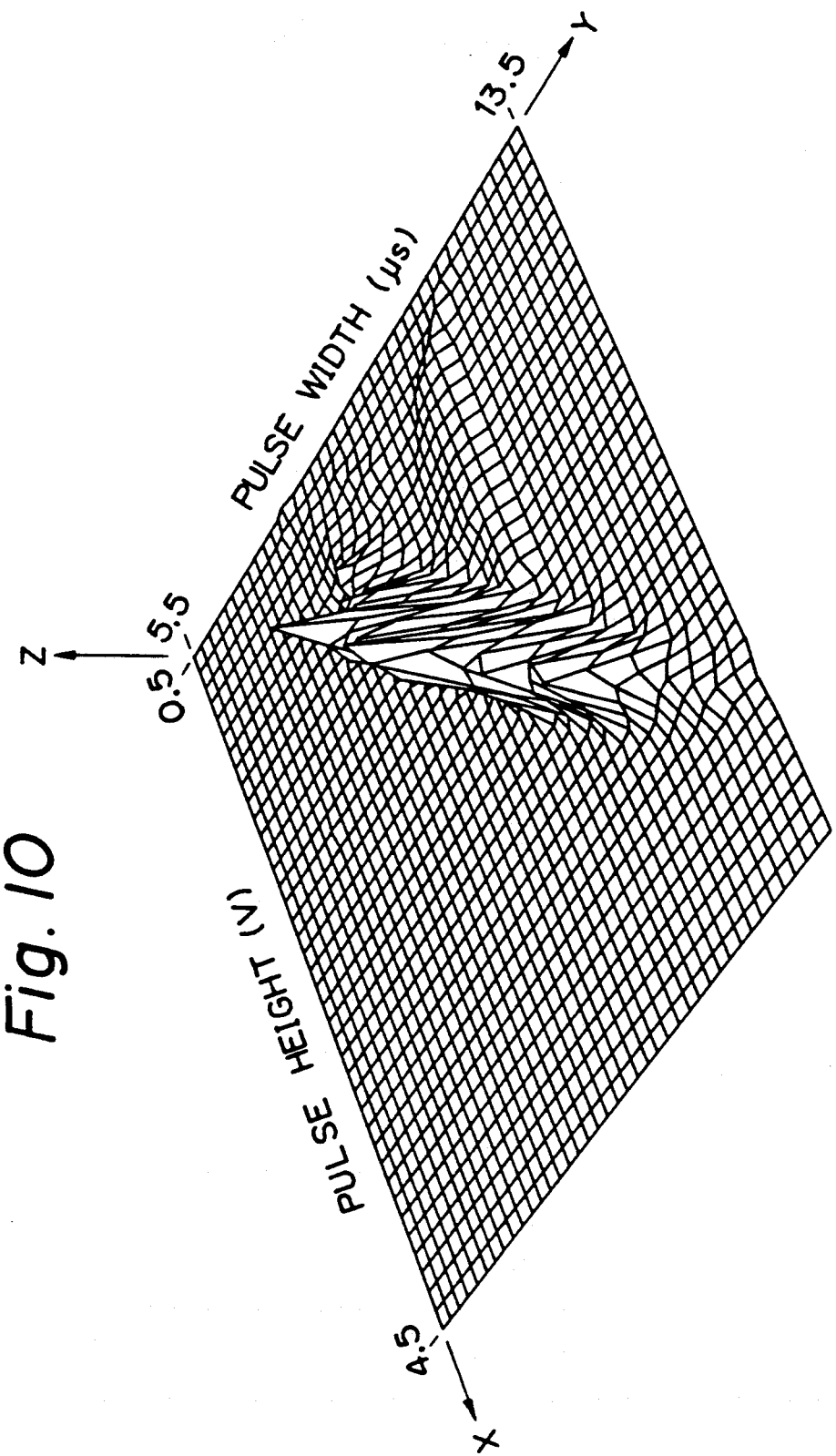
Figure 11:
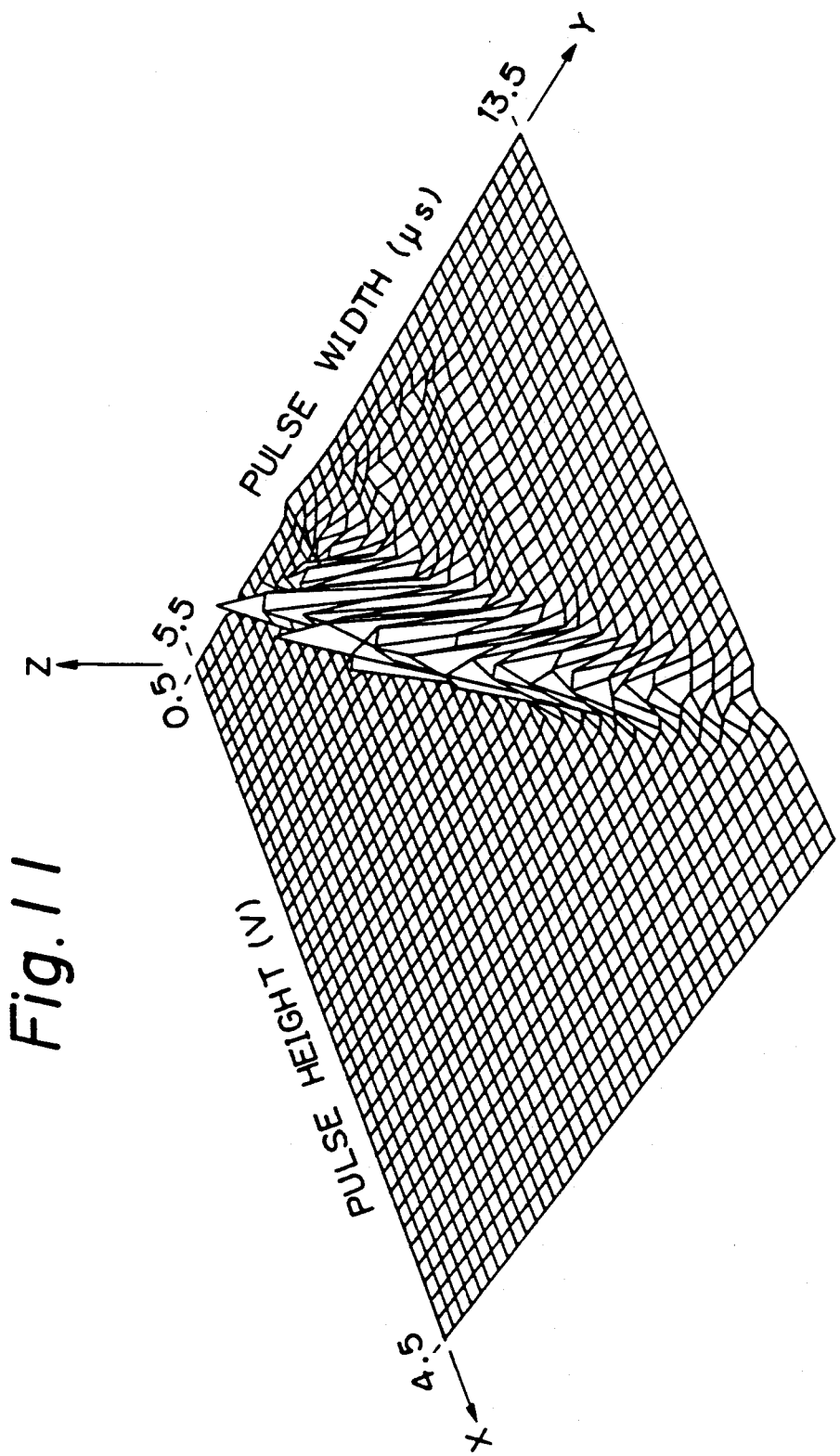

FIGS. 8 through 11 are distributions illustrating the results obtained by measuring samples from patients with microcytic anemia. FIG. 8 is the plot for a patient with the beta-thalassemia trait; the distribution is shifted toward the rear of the grid, in comparison with the distribution for the normal individual. However, the distribution here resembles that for the normal individual in that it is not distorted and generally lies on the aforementioned diagonal of the XY plane. FIG. 9 is the plot for a patient with early iron-deficiency anemia. Though the values of MCV and RDW are very close to those of the patient with the beta-thalassemia trait shown in FIG. 8, the distribution here is broader. FIGS. 8 and 9 are excellent examples for showing that distributions of pulse height and width differ even for samples having substantially the same values of MCV and RDW. These examples demonstrate that observing differences in three-dimensional distributions is useful in distinguishing between patients with iron-deficiency anemia and those with the thalassemia trait. The distribution of FIG. 10 is for a patient with mild chronic iron-deficiency anemia and is shifted to the right of that for the normal individual. The distribution of FIG. 11 is for a patient with severe chronic iron-deficiency anemia and is broader and shifted to the right in comparison with that for the normal individual.

Figure 12:
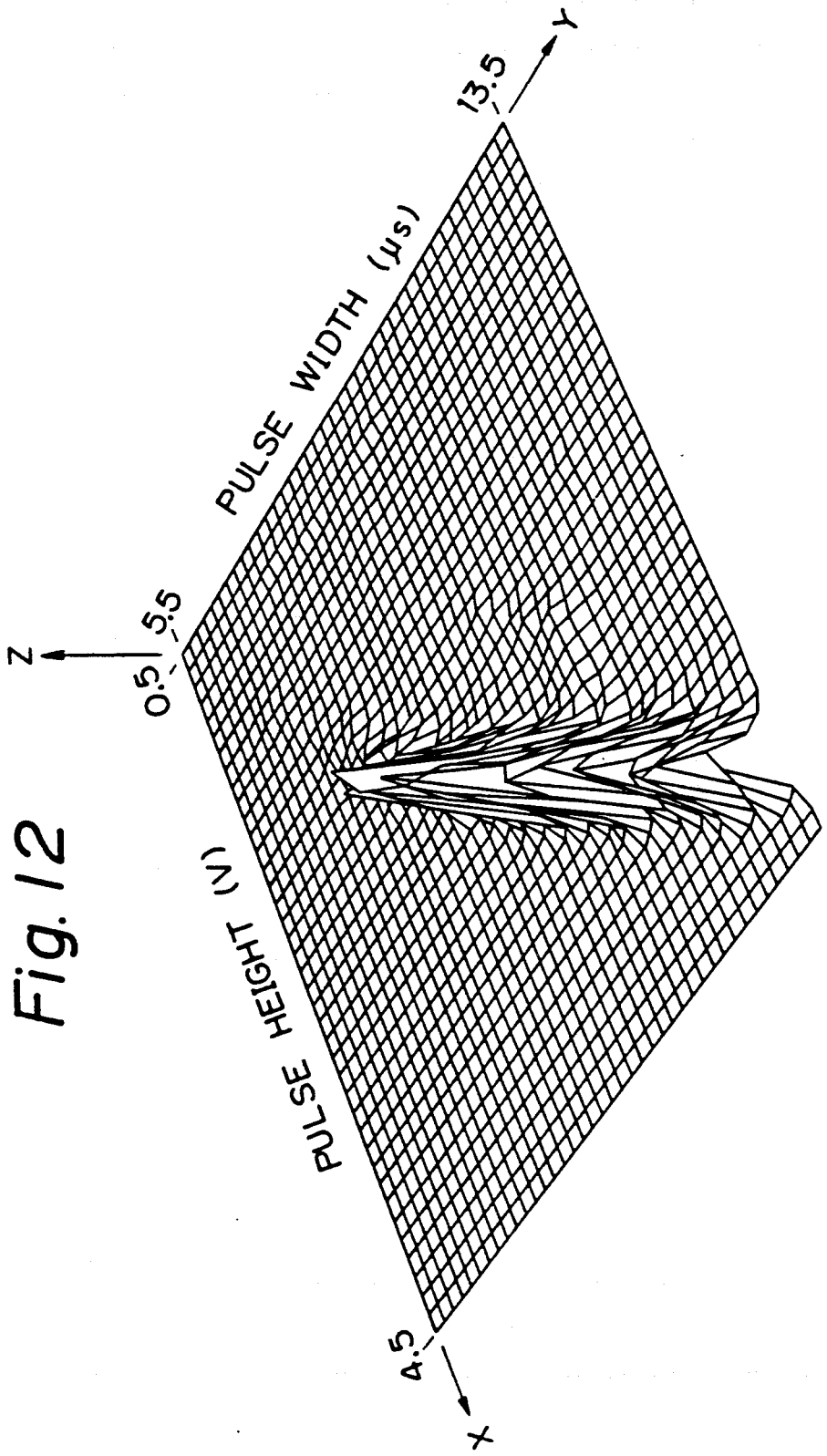
Figure 13:
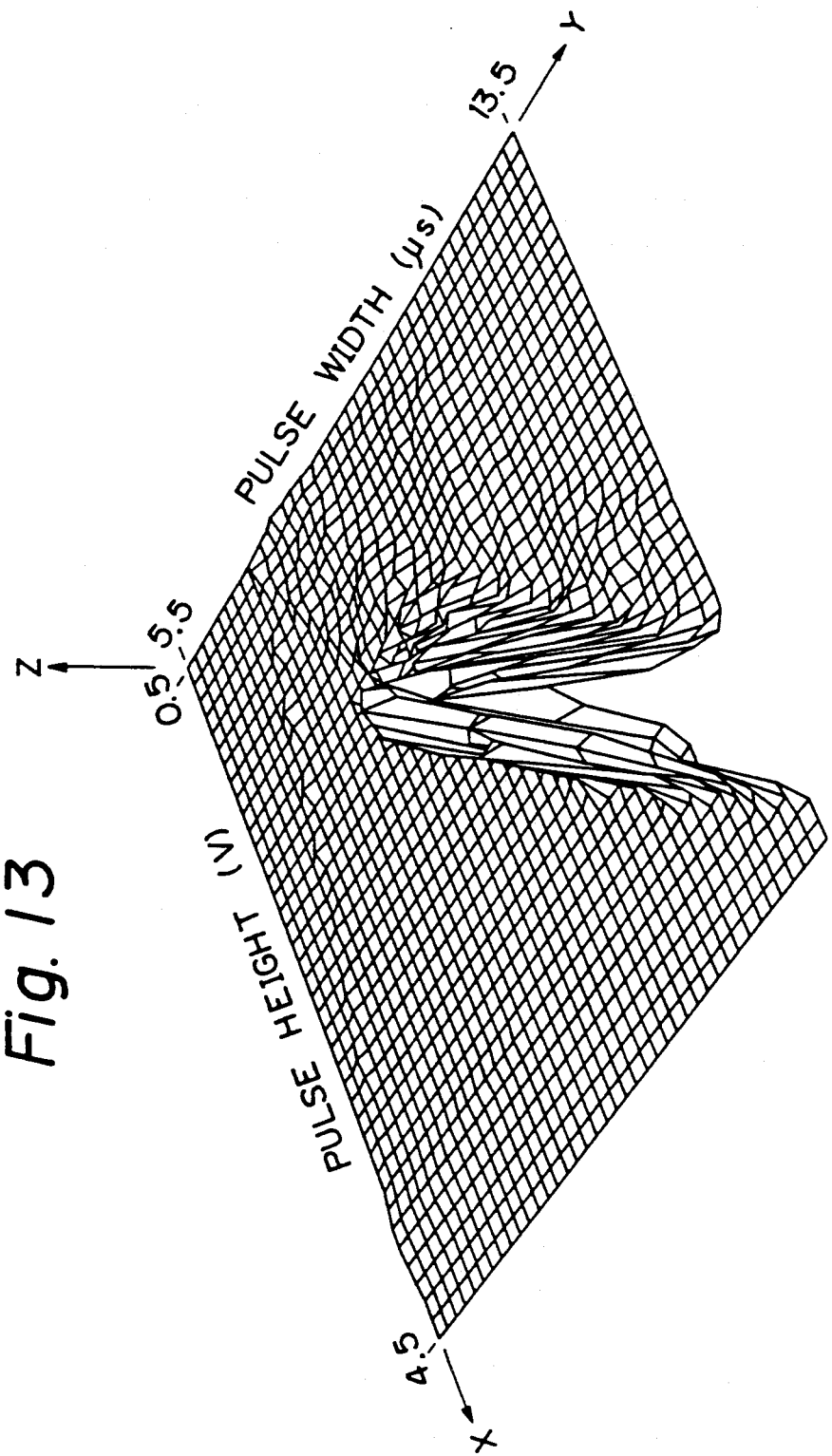
Figure 14:
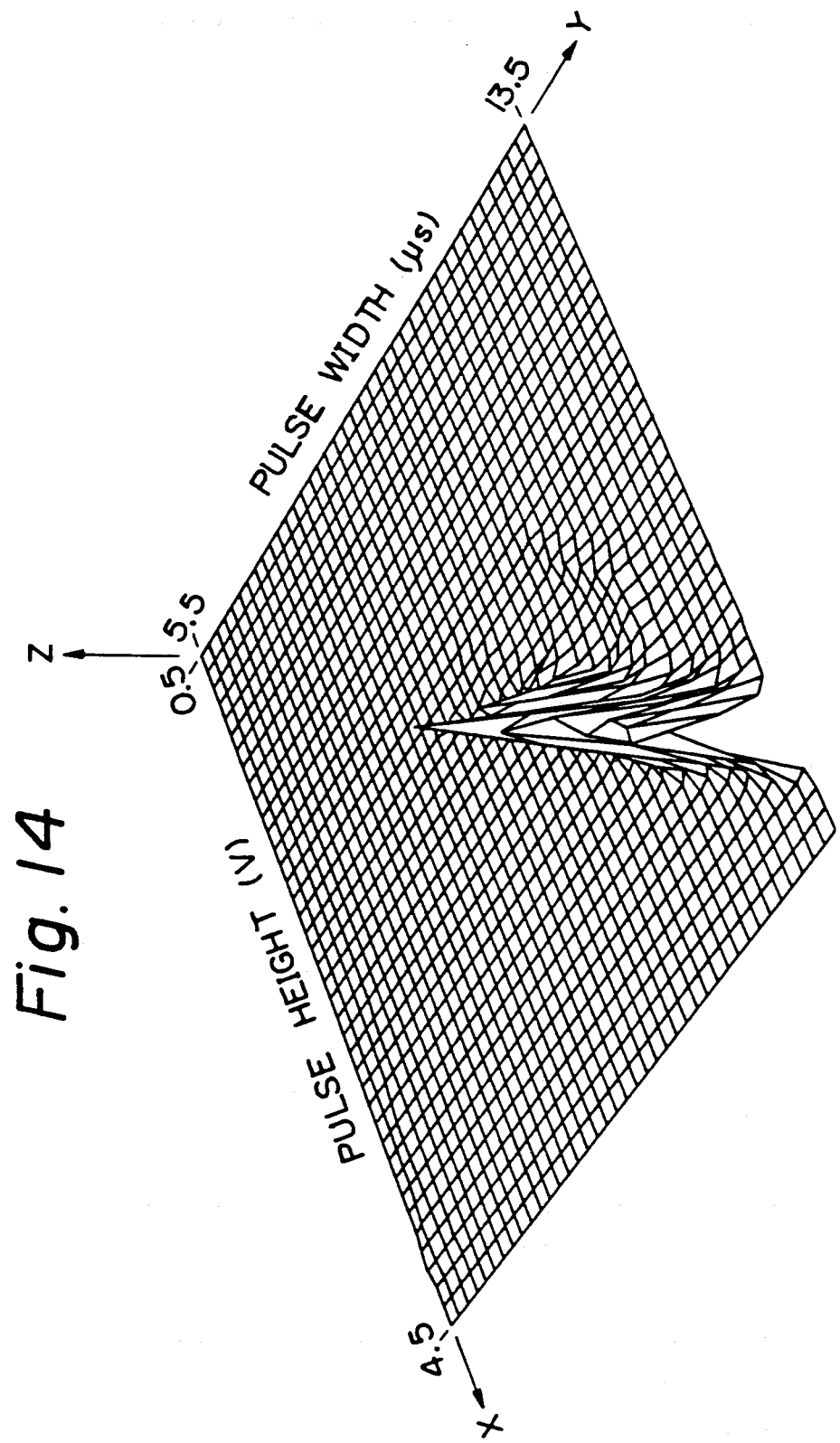

FIGS. 12 through 14 are distributions illustrating the results of measuring samples from patients with macrocytic anemia. Here all of the plots are shifted to the front of the grid because the pulse heights (proportional to particle volume), of the samples are taller than those for the normal individual. The distribution of FIG. 12 is that for a patient with mild folate deficiency anemia and is shifted leftward of the aforementioned diagonal in comparison with the distribution of the normal person. The distribution of FIG. 13 is that for a patient with chronic renal failure receiving cytotoxic chemotherapy. The distribution here is distorted and broadened. FIG. 14 shows the distribution for a patient with an uncommon hemolytic anemia, red cell 5'-nucleotidase deficiency. The distribution is shifted forward but does not appear distorted or displaced to the right or left.

FIGS. 15 through 21 are two-dimensional distributions relating to (a) pulse height, (b) pulse width and (c) pulse height/width ratio. In each view, (a) shows a frequency distribution regarding pulse height (plotted along the horizontal axis) and is well known generally as a particle distribution, (b) shows a frequency distribution regarding pulse width (plotted along the horizontal axis) and is not employed as commonly as a particle distribution, and (c) shows a frequency distribution regarding a parameter which is the height of each pulse, divided by its width (pulse height/width plotted along the horizontal axis). This pulse height/width parameter is a distinguishing parameter first proposed by the present invention for use in the clinical field and affords the possibility of acquiring clinically remarkable information. In each view, MEAN represents the mean of the distribution, STD the standard deviation of the distribution, and # COUNT OFFSCALE the count of particles that cannot be shown on the plot because they are offscale.

Table 1 shows the results of calculating mean value (MEAN), standard deviation (STD), and coefficient of variation (CV) with regard to each of the distributions of pulse height, width and height/width ratio obtained when various samples were measured. Table 1 also shows the names of the disorders associated with the samples and the figure numbers of the three-dimensional distributions and two-dimensional distributions for instances where there are corresponding figures in the drawings. The coefficient of variation (CV) is calculated in accordance with the formula $100 \times STD/MEAN$ (%), as is well known.

Figure 15A:
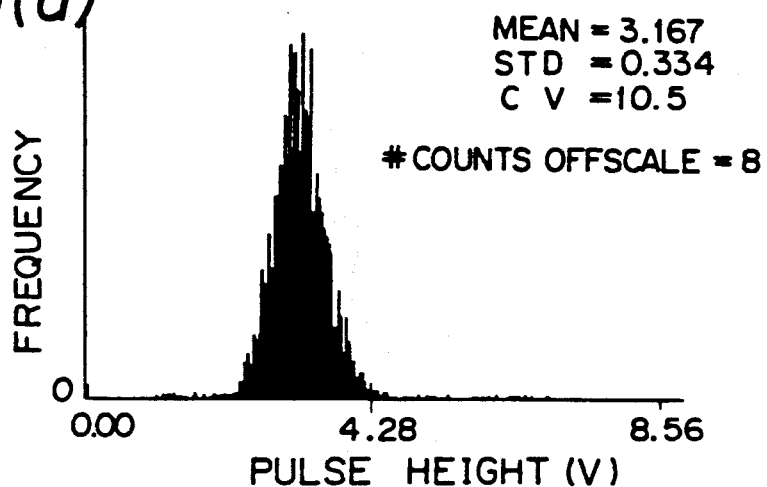
Figure 15B:
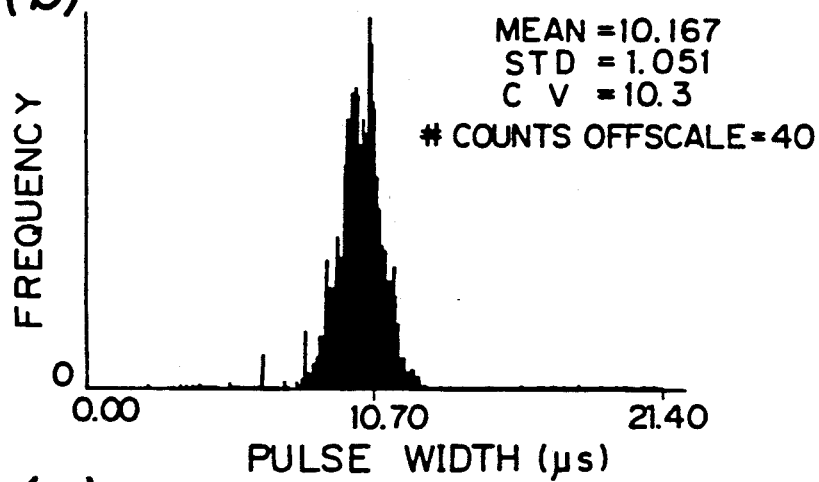
Figure 15C:
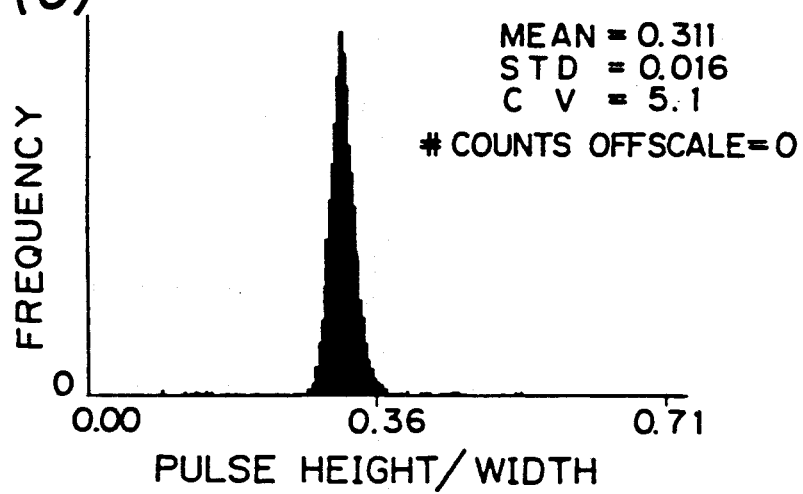
Figure 17A:
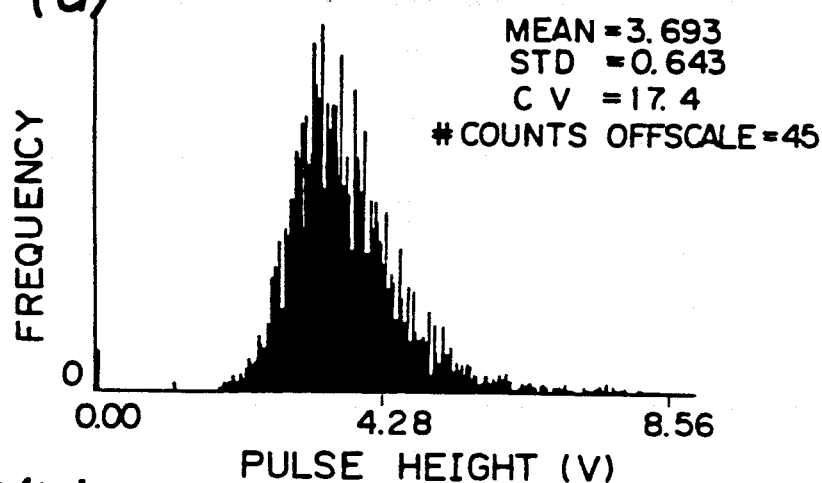
Figure 17B:
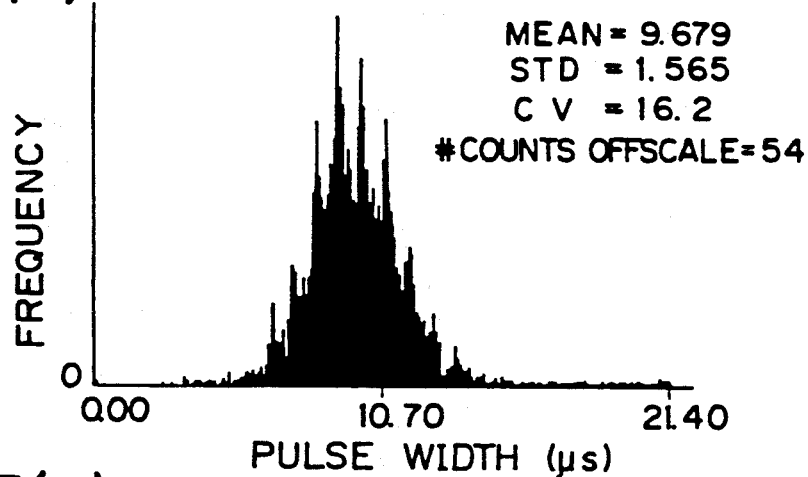
Figure 17C:
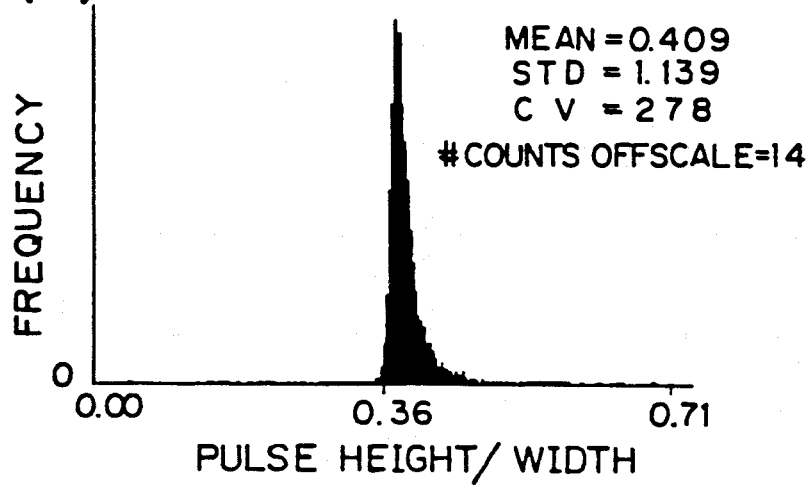

Samples A through D are those of different normal individuals, and FIGS. 5 and 15 are associated with sample C. Samples F and G are those of patients with sickle-cell anemia, and FIGS. 7 and 17 are associated with sample F. The other figures shown in Table 1 similarly correspond to the other samples.

In Table 1, a comparison of the coefficients of variation (CV) of the pulse height or pulse width distributions of the normal individuals with those of the anemic patients indicates that the anemic patients tend to have a somewhat higher CV (i.e. a somewhat larger variation in distribution), but that the difference is not particularly striking. By contrast, when the CV's of the pulse height/width distributions are compared, it is seen that, with the exception of the patients with mild anemia (Sample E), the CV values for the anemic patients are much higher than those for the normal individuals.

It should be noted that since the STD values of the pulse height/width distributions are also higher for the anemic patients than for the normal individuals, this might also serve as useful information. However, using the CV values of these distributions is more useful in that the absolute values of the pulse height/width ratios are unaffected.

Thus, as set forth above, it is demonstrated that information particularly useful in diagnosing anemia is obtained when a height/width parameter, derived from pulse height and width, is selected as a distinguishing parameter and, moreover, the coefficient of variation of the particular distribution is selected as a distribution parameter.

It should be noted that the distinguishing parameter used in the invention can be modified in several ways, such as by adopting pulse width/height as the parameter, though these modifications are not indicated in the illustrated embodiment, and that the types of particles can be changed accordingly, so that the characteristics of each can be accurately analyzed. The invention therefore can be adapted to a variety of applications.

The particle analyzing apparatus of the present invention has the following advantages:

(1) It is possible to obtain information useful in diagnosing anemia by detecting pulse width, which reflects particle characteristics such as cell membrane flexibility and hemoglobin concentration, in addition to pulse height, which relfects particle size.

(2) It is possible to obtain information particularly useful in correctly diagnosing anemia corresponding to a particular disorder by selecting a height/width parameter or width/height parameter, which is derived from pulse height and width, as a distinguishing parameter, and selecting the coefficient of variation of the distributions of these distinguishing parameters as a distribution parameter.

(3) If the apparatus of the invention is adapted to provide three-dimensional distribution plots in which pulse height and width serve as the parameters, then this will make it possible to identify iron-deficiency anemia and thalassemia, which are two types of anemia that cannot be distinguished from each other in the prior art merely by using plots of particle distribution. Thus, the inventive apparatus in this form is capable of contributing significantly to clinical diagnosis.

As many apparently widely different embodiments of the present invention can be made without departing from the spirit and scope thereof, it is to be understood that the invention is not limited to the specific embodiments thereof, except as defined in the appended claims.

TABLE 1

Figure 16A:
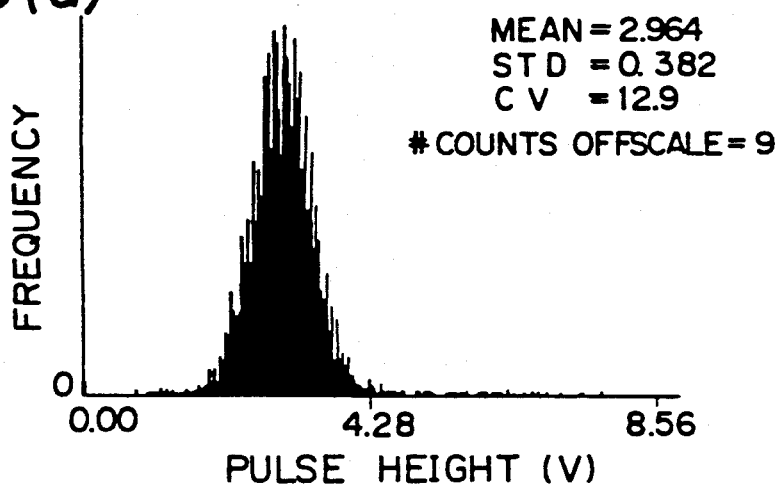
Figure 16B:
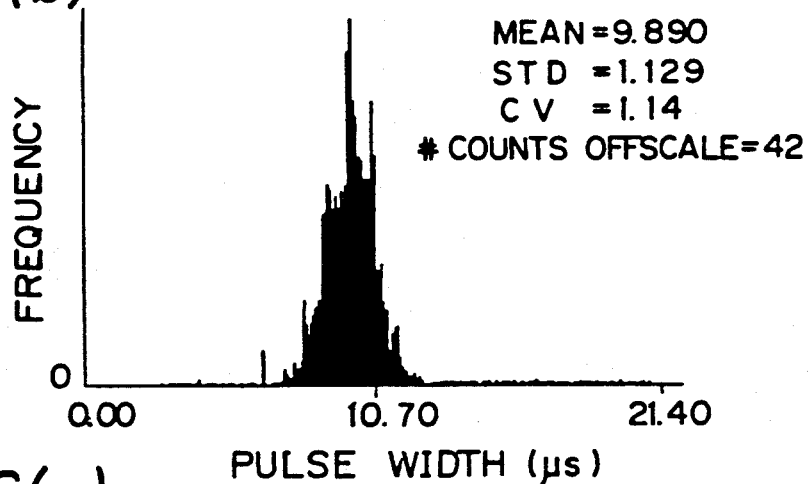
Figure 16C:
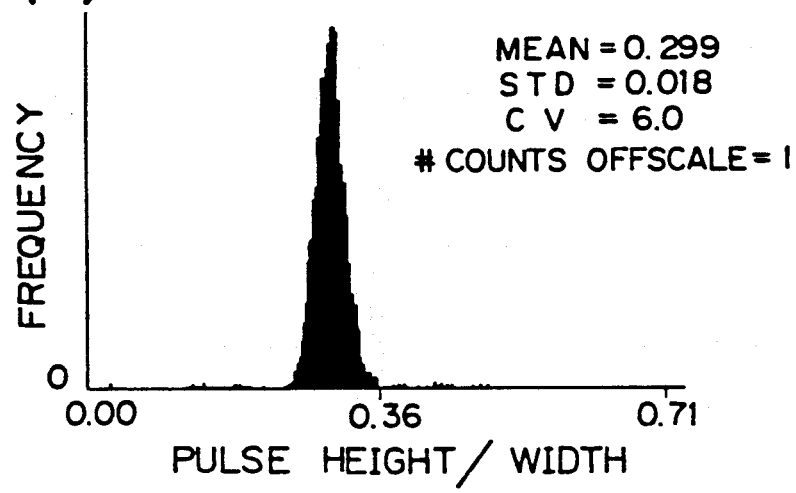
Figure 18A:
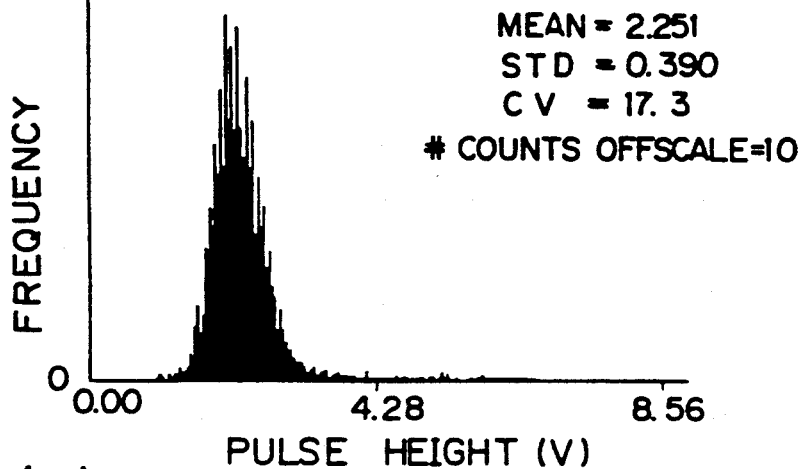
Figure 18B:
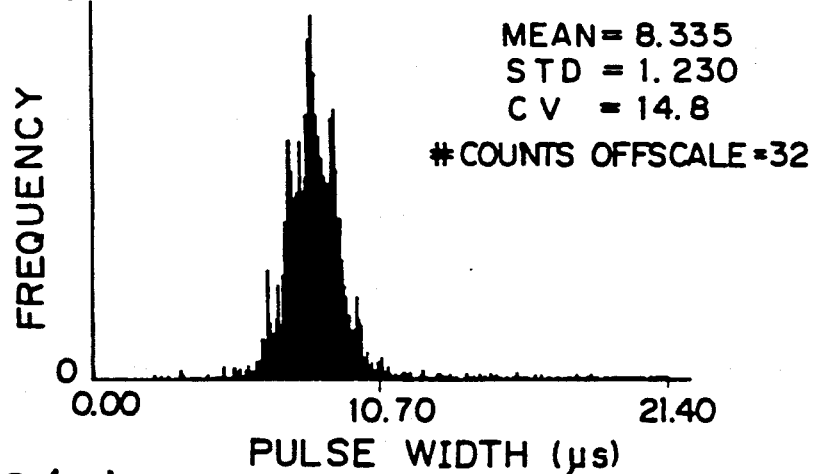
Figure 18C:
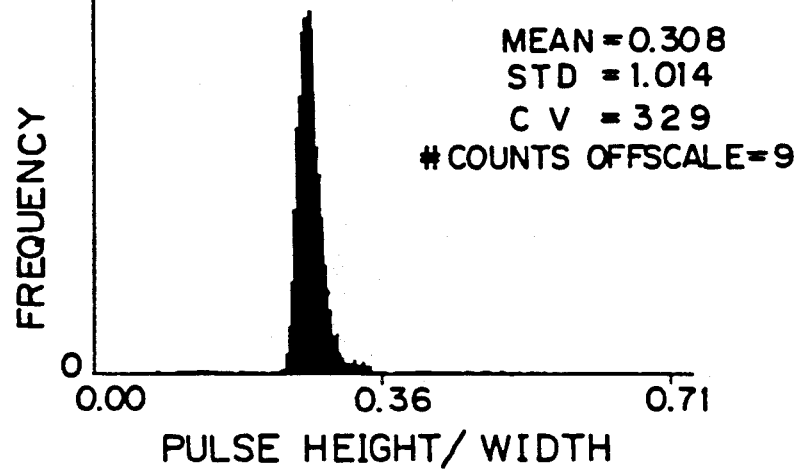
Figure 19A:
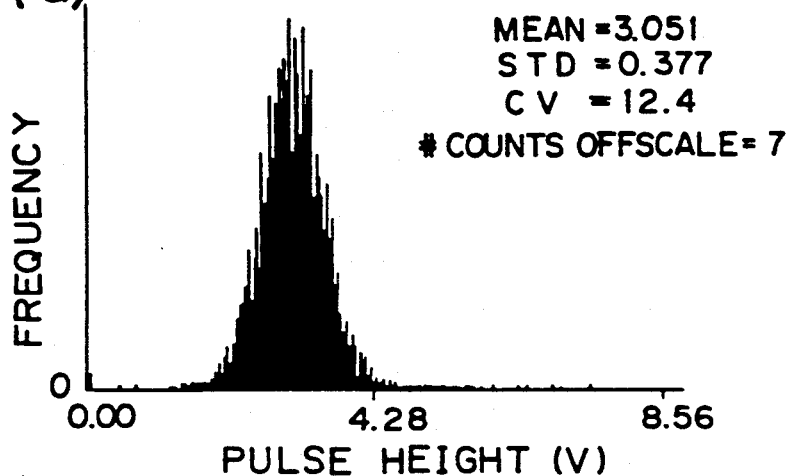
Figure 19B:
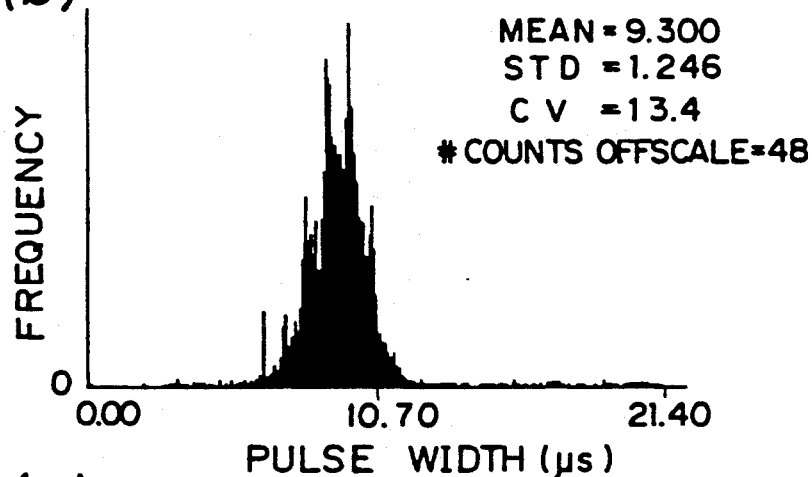
Figure 19C:
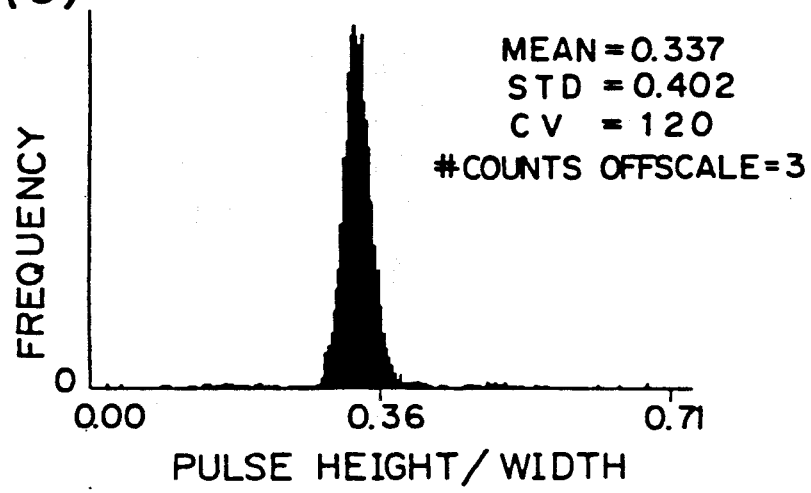
Figure 20A:
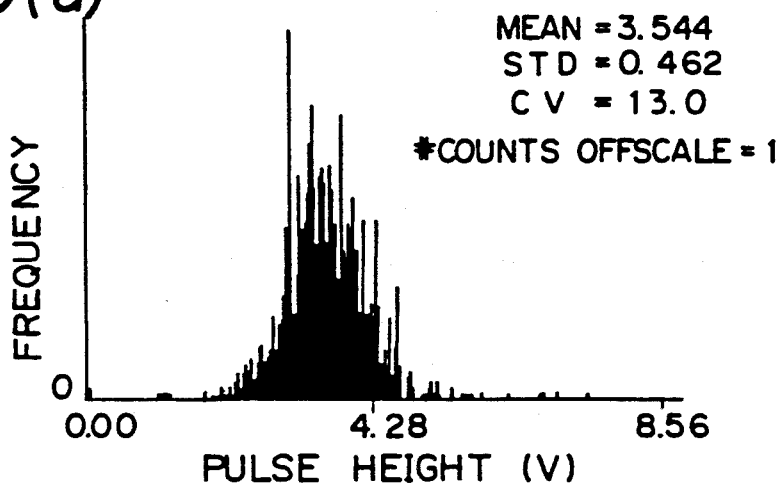
Figure 20B:
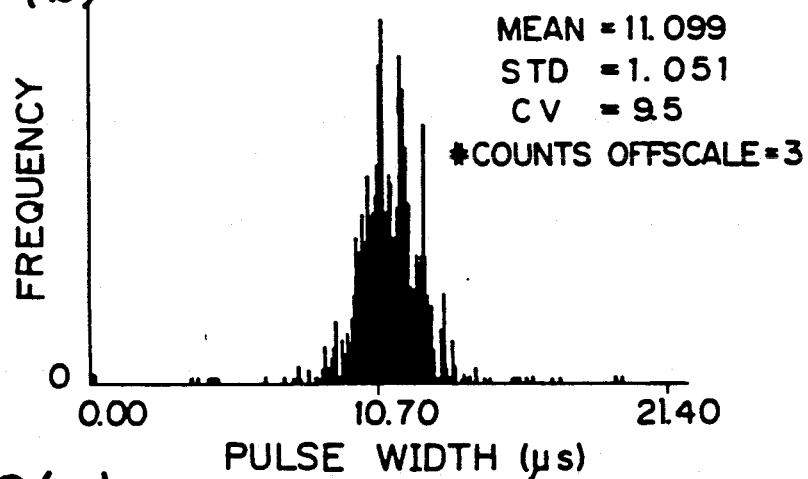
Figure 20C:
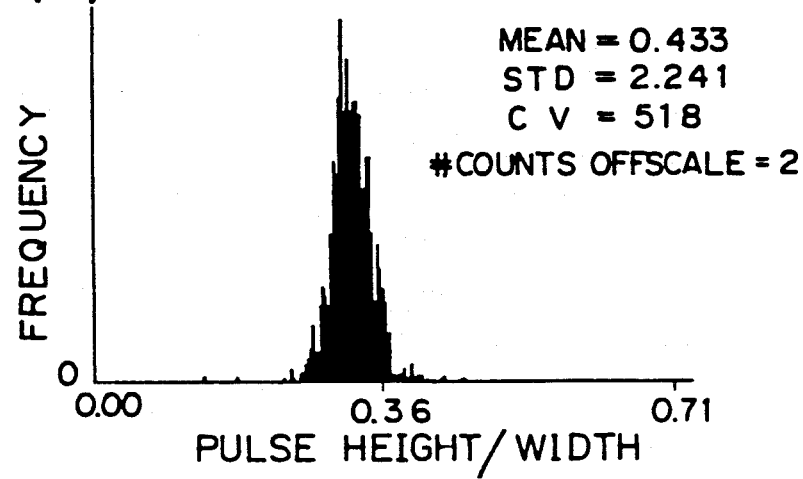
Figure 21A:
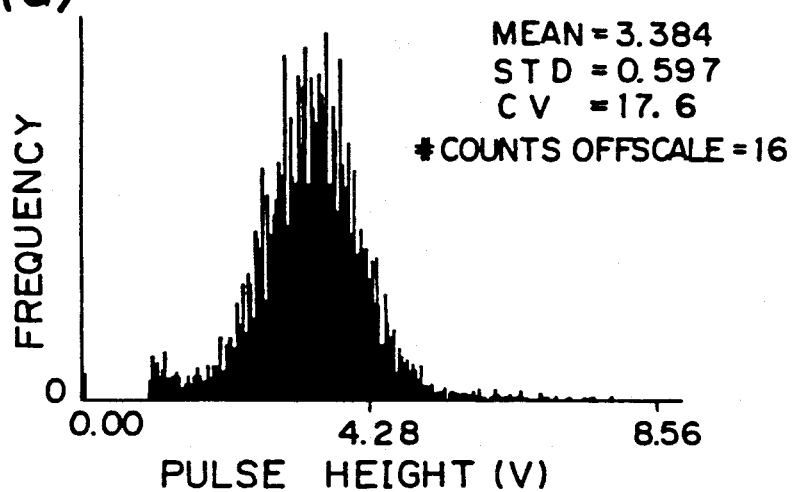
Figure 21B:
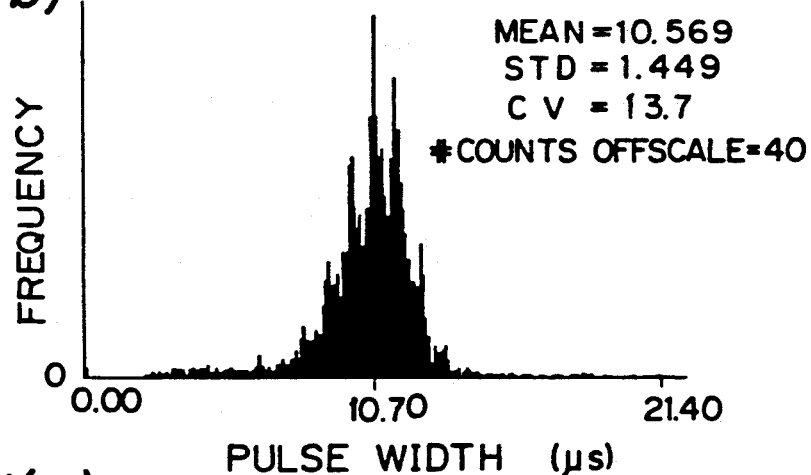
Figure 21C:
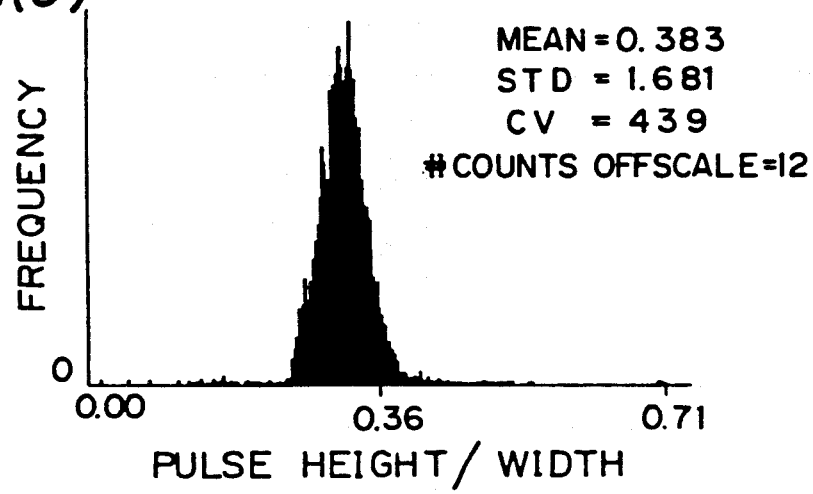

| Sample | 3-D Dist. | 2-D Dist. | Pulse height MEAN | Pulse height STD | Pulse height CV | Pulse width MEAN | Pulse width STD | Pulse width CV | Pulse height/width MEAN | Pulse height/width STD | Pulse height/width CV | Remarks |
|--------|-----------|-----------|------|------|------|------|------|------|------|------|-----|---------|
| A | — | — | 2.745 | 0.363 | 13.2 | 9.571 | 1.207 | 12.6 | 0.287 | 0.018 | 6.3 | Normal patient |
| B | — | — | 2.839 | 0.343 | 12.1 | 9.674 | 1.070 | 11.1 | 0.293 | 0.018 | 6.1 | Normal patient |
| C | FIG. 5 | FIG. 15 | 3.167 | 0.334 | 10.5 | 10.167 | 1.051 | 10.3 | 0.311 | 0.016 | 5.1 | Normal patient |
| D | — | — | 3.449 | 0.392 | 11.4 | 10.414 | 1.299 | 12.5 | 0.332 | 0.019 | 5.7 | Normal patient |
| E | FIG. 6 | FIG. 16 | 2.964 | 0.382 | 12.9 | 9.890 | 1.129 | 11.4 | 0.299 | 0.018 | 6.0 | Patient with mild anemia caused by chronic disorder |
| F | FIG. 7 | FIG. 17 | 3.693 | 0.643 | 17.4 | 9.679 | 1.565 | 16.2 | 0.409 | 1.139 | 278 | Patient with sickle cell anemia |
| G | — | — | 3.442 | 0.545 | 15.9 | 9.775 | 1.398 | 14.3 | 0.373 | 0.988 | 265 | Patient with sickle cell anemia |
| H | FIG. 8 | FIG. 18 | 2.251 | 0.390 | 17.3 | 8.335 | 1.230 | 14.8 | 0.308 | 1.014 | 329 | Patient with beta-thalassemia trait |
| I | FIG. 10 | FIG. 19 | 3.051 | 0.377 | 12.4 | 9.300 | 1.246 | 13.4 | 0.337 | 0.402 | 120 | Patient with mild chronic iron deficiency |
| J | FIG. 12 | FIG. 20 | 3.544 | 0.462 | 13.0 | 11.099 | 1.051 | 9.5 | 0.433 | 2.241 | 518 | Patient with mild folate deficiency anemia |
| K | FIG. 13 | FIG. 21 | 3.384 | 0.597 | 17.6 | 10.569 | 1.449 | 13.7 | 0.383 | 1.681 | 439 | Patient with chronic renal failure receiving cytotoxic chemotherapy |

What is claimed is:

1. A particle analyzing apparatus which detects a change in a signal produced by a particle floating in an electrolytic suspension as the particle passes through a detector aperture, comprising:

particle detecting means for generating pulses corresponding to individual particles in a sample;

means for detecting height and width of individual generating pulses corresponding to said individual particles;

means for calculating as a distinguishing parameter a ratio of the detected pulse height to the detected pulse width;

means for calculating a coefficient of variation of the ratio of the pulse height to the pulse width as a distribution parameter of said distinguishing parameter; and data means for displaying and recording at least one of said pulse data and calculated data, wherein said pulse data comprises the detecting pulse height and width and the calculated data comprises the calculated ratio and calculated coefficient of variation.

2. An apparatus according to claim 1, further comprising three-dimensional display data processing means operatively associated with said pulse height and width detecting means and said data means for providing plots of three-dimensional distributions in which a frequency histogram is expressed in a direction perpendicular to a plane having two axes along which pulse height and width are plotted.

* * * * *

UNITED STATES PATENT AND TRADEMARK OFFICE
CERTIFICATE OF CORRECTION

PATENT NO. : 5,059,395
DATED : October 22, 1991
INVENTOR(S) : Brittenham et al.

It is certified that error appears in the above-identified patent and that said Letters Patent is hereby corrected as shown below:

On the title page, Item

[75] Inventors: change "Hyogo, Japan" to --Hyogo-ken, Japan--.
[73] Assignee, change "Kobe, Japan" to --Hyogo-ku, Kobe-shi, Hyogo-ken, Japan--.

Column 2, line 46, change "sheathflow" to --sheath-flow--.
Column 2, line 46, change "adpoted" to --adopted--.
Column 7, line 46, change "relfects" to --reflects--.

Signed and Sealed this

Twentieth Day of April, 1993

Attest:

MICHAEL K. KIRK

*Attesting Officer*   Acting Commissioner of Patents and Trademarks